United States Patent
Moszner et al.

(10) Patent No.: US 11,013,669 B2
(45) Date of Patent: May 25, 2021

(54) DENTAL MATERIALS WITH LIGHT-INDUCED REVERSIBLE COLORING

(71) Applicant: Ivoclar Vivadent AG, Schaan (LI)

(72) Inventors: Norbert Moszner, Mauren (LI); Thorsten Bock, Feldkirch (AT); Martina Hauner-Westphal, Feldkirch (AT); Alexandros Gianasmidis, Balgach (CH); Iris Lamparth, Grabs (CH); Bernd Strehmel, Krefeld (DE); Thomas Brömme, St. Pantaleon (CH)

(73) Assignee: Ivoclar Vivadent AG, Schaan (LI)

( * ) Notice: Subject to any disclaimer, the term of this patent is extended or adjusted under 35 U.S.C. 154(b) by 12 days.

(21) Appl. No.: 16/063,846

(22) PCT Filed: Dec. 9, 2016

(86) PCT No.: PCT/EP2016/080529
§ 371 (c)(1),
(2) Date: Jun. 19, 2018

(87) PCT Pub. No.: WO2017/108456
PCT Pub. Date: Jun. 29, 2017

(65) Prior Publication Data
US 2019/0008728 A1    Jan. 10, 2019

(30) Foreign Application Priority Data

Dec. 21, 2015   (EP) .................... 15201791

(51) Int. Cl.
| | |
|---|---|
| A61K 6/00 | (2020.01) |
| C09K 9/02 | (2006.01) |
| A61K 6/66 | (2020.01) |
| A61K 6/62 | (2020.01) |
| A61K 6/887 | (2020.01) |

(52) U.S. Cl.
CPC ............. *A61K 6/66* (2020.01); *A61K 6/62* (2020.01); *A61K 6/887* (2020.01); *C09K 9/02* (2013.01); *C09K 2211/1018* (2013.01)

(58) Field of Classification Search
CPC .... A61K 6/0052; A61K 6/0061; A61K 6/083; A61K 6/00; C09K 9/02; C09K 2211/1018
See application file for complete search history.

(56) References Cited

U.S. PATENT DOCUMENTS

| | | | | |
|---|---|---|---|---|
| 5,698,020 A | * | 12/1997 | Saiz ............... | A61K 6/083 106/35 |
| 2011/0216273 A1 | * | 9/2011 | He ................ | C09K 19/0403 349/96 |
| 2014/0329929 A1 | * | 11/2014 | Moszner ......... | A61K 6/0002 523/116 |

FOREIGN PATENT DOCUMENTS

CA   2635037 A1 * 10/2008 ............ C09B 49/00

OTHER PUBLICATIONS

Yuri Boiko, Improvement of thermal stability in photochromic holograms, Optics Letters / vol. 34, No. 8 / Apr. 15, 2009. (Year: 2009).*
Masahiro Irie, Diarylethenes for Memories and Switches, Chem. Rev. 2000, 100, 1685-1716. (Year: 2000).*
Liang Shen, Cha Ma, Shouzhi Pu, Chuanjie Cheng, Jingkun Xu, Long Li and Changqing Fu,Synthesis and properties of novel photochromic poly(methyl methacrylate-co-diarylethene)s, New J. Chem., 2009, 33, 825-830. (Year: 2009).*
Corns, S.N. et al., "Industrial organic photochromic dyes," Society of Dyers and Colourists, Coloration Technology, 125, pp. 249-261, 2009.
Irie, M., "Diarylethenes for Memories and Switches," Chem. Rev., 100, pp. 1685-1716, 2000.
Boiko, Y., "Improvement of thermal stability in photochromic holograms," Optics Letters, vol. 34, No. 8, pp. 1279-1281, Apr. 15, 2009.
International Preliminary Report on Patentability of PCT/EP2016/080529, dated Jun. 26, 2018, 14 pages.

* cited by examiner

*Primary Examiner* — Bijan Ahvazi
(74) *Attorney, Agent, or Firm* — Ann M. Knab; Thad McMurray

(57) ABSTRACT

The invention relates to a radically polymerizable dental material having photochromic properties, which contains at least one compound of formula (I) and optionally radically polymerizable monomers, an initiator for radical polymerization and other components.

11 Claims, No Drawings

DENTAL MATERIALS WITH LIGHT-INDUCED REVERSIBLE COLORING

CROSS-REFERENCE TO RELATED APPLICATIONS

This application is a National Stage application of International patent application PCT/EP2016/080529 filed on Dec. 9, 2016, which claims priority to European patent application No. 15201791.9 filed on Dec. 21, 2015, the disclosures of which are incorporated herein by reference in their entirety.

FIELD OF THE INVENTION

The present invention relates to heat- and/or light-curing compositions with light-induced reversible colouring, such as polymerization resins and composites, which are suitable in particular as dental filling composites, veneering materials, dental adhesives and dental coating materials, as well as for the production of inlays and onlays.

BACKGROUND OF THE INVENTION

In the case of plastics, colourants are added to the polymer as additives to set the desired colour and transparency. A distinction is made between dyes and pigments. Dyes have an organic nature and are usually soluble in organic solvents, while pigments are solid particles with particle sizes between approx. 0.01 and approx. 1 µm. Pigments are divided into organic and inorganic pigments (cf. Taschenbuch der Kunststoff-Additive, Ed. R. Gächter, H. Müller, 3rd edition, Carl Hanser Verlag, Munich and Vienna 1989, 663-736). In the case of dental materials used in dentistry and in particular in the case of highly aesthetic filling composites mixtures of different inorganic pigments are used to set the colour, which are characterized by low solubility in organic solvents and fats as well as by a very good colour stability. In addition to the permanent colouration of dental materials, it is advantageous in some situations to be able to make the dental material more visible temporarily by reversible colouring. Examples of this are a reversible colouring for the identification of thin layers, such as in the case of tooth surfaces treated with adhesive or cement surpluses, as well as for making fissure sealants visible.

EP 0 744 172 A1 discloses photochromic dental materials which contain a photochromic material such as for example a photochromic dye, a photochromic glass, a photochromic ceramic and/or a photochromic glass ceramic. By brief irradiation with light the photochromic dental material can be converted to a coloured state which makes a better differentiation from the natural tooth structure possible. A disadvantage is that the subsequent decolouration sometimes extends over several hours, which can impair the light-induced material hardening. In addition, the dentist cannot control the ultimate colouring of the restoration in one session.

A distinction is made between photochromic substances of the T-type, in which the reverse reaction proceeds predominantly thermally after the irradiation has ended, and substances of the P-type, in which the reverse reaction proceeds predominantly photochemically, i.e. is triggered by light of a different wavelength (cf. S. N. Corns, A. M. Partingtom, A. D. Towns, Color. Technol. 125 (2009) 249-261). Examples of photochromic substances of the P-type are diarylethenes with heterocyclic aryl groups (cf. M. Irie, Chem. Rev. 100 (2000) 1685-1716). The use of photochromic diarylethenes in dental materials is not known according to the state of the art.

SUMMARY OF THE INVENTION

The object of the invention is to provide materials for dental applications, the colour of which can be reversibly altered by irradiation with light and which do not have the disadvantages associated with the state of the art.

DETAILED DESCRIPTION

The object is achieved according to the invention by radically polymerizable materials which contain at least one photochromic diarylethene according to M. Irie, Chem. Rev. 100 (2000) 1685-1716).

Radically polymerizable dental materials which contain a compound according to general formula I are preferred:

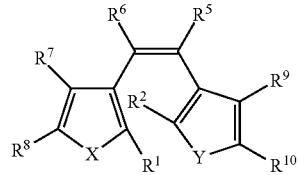

Formula I in which the variables have the following meanings:

X, Y independently of each other in each case are O, S, Se, $CH_2$, N—$R^{11}$ or $CR^{12}R^{13}$, wherein $R^{11}$ to $R^{13}$ independently of each other in each case are a branched or unbranched $C_1$-$C_{16}$ alkyl radical, aryl or —$CH_2$-aryl, wherein X and Y preferably have the same meaning;

$R^1$, $R^2$ independently of each other in each case are a branched or unbranched $C_1$-$C_3$ alkyl radical, wherein these alkyl radicals can be substituted by one or more fluorine atoms;

$R^5$; $R^6$ independently of each other in each case are halogen, CN, COOH, COO$R^4$, $CH_2$OH, CO—$NH_2$, $CH_2$—$NH_2$, wherein $R^4$ is a $C_1$-$C_6$ alkyl radical, aryl or alkyl-aryl, or $R^5$ and $R^6$ together form a —$(CH_2)_n$—, —C(=O)—O—C(=O)— or —C(=O)—$NR^3$—C(=O)— group, wherein n is 3 or 4 and $R^3$ is H, a $C_1$-$C_6$ alkyl radical, aryl or alkyl-aryl and wherein in the —$(CH_2)_n$— group one or more, preferably all H atoms can be replaced by F;

$R^{7-10}$ independently of each other in each case are H, a $C_1$-$C_{12}$ alkyl radical, which can be interrupted by O, —O—C(=O)—NH— or phenylene, or an aromatic $C_6$-$C_{10}$ hydrocarbon radical, wherein these radicals in each case can carry a radically polymerizable group, or $R^7$ and $R^8$ and/or $R^9$ and $R^{10}$, together with the C atoms to which they are bonded, form a benzene ring, which can be unsubstituted or which can carry 1 to 4 substituents, which are selected from halogen, CN, —CO-aryl, —CO—$CH_2$-aryl, —CO—O-aryl, —CO—O—$CH_2$-aryl, branched or unbranched $C_1$-$C_{16}$ alkyl radicals, —O—alkyl, —CO-alkyl and —CO—O-alkyl, wherein alkyl in each case stands for a branched or unbranched $C_1$-$C_{16}$ alkyl radical and wherein all alkyl radicals can be substituted by one or more fluorine atoms;

wherein according to the invention those compounds which contain at least one radically polymerizable group are preferred.

Formula (I) and the other formulae shown herein cover all stereoisomeric forms as well as mixtures of different stereoisomeric forms, such as e.g. racemates. The formulae cover only those compounds that are compatible with the chemical valence theory. The indication that a radical can be interrupted by a hetero atom such as O is to be understood to mean that the O atoms are inserted into the carbon chain or the carbon ring of the radical, i.e. are bordered on both sides by carbon atoms. The number of hetero atoms is therefore at least 1 less than the number of carbon atoms, and the hetero atoms cannot be terminal. In the case of hydrocarbon radicals which contain carbon and hetero atoms, the number of hetero atoms is always less than the number of carbon atoms regardless of substituents. $C_1$ radicals cannot be interrupted.

The term aryl herein stands in each case for an aromatic hydrocarbon radical, preferably a phenyl radical, which can be substituted and preferably is unsubstituted.

Preferred polymerizable groups which can be present as substituents in the radicals R are vinyl, styryl, acrylate ($CH_2$=CH—CO—O—), methacrylate ($CH_2$=C($CH_3$)—CO—O—), acrylamide ($CH_2$=CH—CO—$NR^{14}$— where $R^{14}$=H or $C_1$-$C_8$ alkyl), methacrylamide ($CH_2$=C($CH_3$)—CO—NH—), particularly preferably (meth)acrylate, methacrylamide and/or N-alkylacrylamide.

Compounds according to Formula I in which the variables have the following meanings are preferred:
X, Y independently of each other are O, S or N—$R^{11}$, wherein $R^{11}$ is a branched or unbranched $C_1$-$C_6$ alkyl radical;
$R^1$, $R^2$ independently of each other in each case are a $C_1$-$C_2$ alkyl radical, wherein these alkyl radicals can be substituted by one or more fluorine atoms;
$R^5$; $R^6$ together form a —$(CH_2)_n$— group, wherein n is 3 or 4 and wherein in the —$(CH_2)_n$— group one or more, preferably all H atoms can be replaced by F;
$R^{7-10}$ independently of each other in each case are H or a $C_1$-$C_6$ alkyl radical, which can be interrupted by O or —O—C(=O)—NH—, wherein one or more H atoms can be substituted by fluorine atoms and wherein 1 or 2 of the radicals $R^{7-10}$ carry a radically polymerizable group, preferably a (meth)acrylate group.

Compounds according to Formula I in which the variables have the following meanings are particularly preferred:
X, Y in each case are S;
$R^1$, $R^2$ in each case are methyl;
$R^5$; $R^6$ together form a —$(CH_2)_n$— group, wherein n is 3 and wherein preferably all H atoms are replaced by F;
$R^7$, $R^9$ independently of each other in each case are H or a $C_1$-$C_3$ alkyl radical;
$R^8$, $R^{10}$ independently of each other in each case are a $C_1$-$C_6$ alkyl radical, which can be interrupted by O or —O—C(=O)—NH— and which carries a terminal radically polymerizable group, preferably a methacrylate group.

Furthermore, those compounds of Formula I in which $R^7$ and $R^8$ stand for a group with Formula Ia and $R^9$ and $R^{10}$ stand for a group with Formula Ib are preferred:

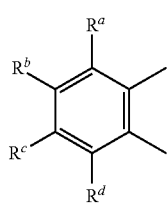

Formula Ia

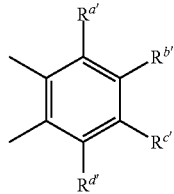

Formula Ib

Compounds of this type can be represented by the following Formula (II):

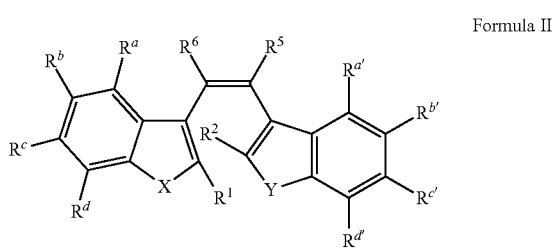

Formula II $R^a$, $R^b$, $R^c$, $R^d$ and $R^{a'}$, $R^{b'}$, $R^{c'}$, $R^{d'}$ independently of each other in each case mean:
H, halogen, CN, a branched or unbranched $C_1$-$C_{16}$ alkyl radical, —O-alkyl, —CO-alkyl, —CO—O-alkyl, wherein alkyl in each case stands for a branched or unbranched $C_1$-$C_{16}$ alkyl radical and wherein all alkyl radicals can be substituted by one or more fluorine atoms, —CO-aryl, —CO—$CH_2$-aryl, —CO—O-aryl, —CO—O—$CH_2$-aryl;
wherein the radicals $R^a$, $R^b$, $R^c$, $R^d$ or $R^{3'}$, $R^{b'}$, $R^{c'}$, $R^{d'}$ can be linked to each other, forming one or more non-aromatic or preferably aromatic rings and in particular annulated aromatic ring systems, which preferably have 2 to 5 rings, wherein the rings or ring systems can be substituted or preferably unsubstituted.

The remaining variables have the above-specified meanings.

A preferred group of compounds of Formula II are those compounds in which the variables have the following meanings, which can be chosen independently of each other:
X, Y independently of each other in each case are 0, N—$R^{11}$, wherein $R^{11}$ is a branched or unbranched $C_1$-$C_{16}$ alkyl radical, N-aryl or N—$CH_2$-aryl;
$R^1$, $R^2$ independently of each other in each case are a branched or unbranched $C_1$-$C_6$ alkyl radical, wherein the alkyl radicals can be substituted by one or more fluorine atoms;
$R^5$, $R^6$ independently of each other in each case are halogen, CN, COOH, $COOR^4$, wherein $R^4$ is H, alkyl, aryl, alkylaryl, $CH_2OH$, CO—$NH_2$ or $CH_2$—$NH_2$, or $R^5$ and $R^6$ together form a —C(=O)—O—C(=O)—, —C(=O)—$NR^3$—C(=O)— or —$(CH_2)_n$— group, wherein n is 3 or 4 and one or more, preferably all H atoms can be replaced by F and wherein $R^3$ is H or a $C_1$-$C_6$ alkyl radical, aryl or alkyl-aryl;
$R^a$, $R^b$, $R^c$, $R^d$ and $R^{a'}$, $R^{b'}$, $R^{c'}$, $R^{d'}$ independently of each other are
H, halogen, a branched or unbranched $C_1$-$C_{16}$ alkyl radical, —O-alkyl, —CO—O-alkyl, wherein alkyl in each case stands for a branched or unbranched $C_1$-$C_{16}$ alkyl radical and wherein all alkyl radicals can be substituted by one or more fluorine atoms, —CO-aryl, —CO—CH$_2$-aryl, —CO—O-aryl, —CO—O—CH$_2$-aryl;
wherein the radicals R$^a$, R$^b$, R$^c$, R$^d$ and/or the radicals R$^{a\prime}$, R$^{b\prime}$, R$^{c\prime}$, R$^{d\prime}$ can be linked to each other, forming one or more aromatic rings, preferably an annulated aromatic ring system with 2 to 3 rings, wherein the rings or ring systems can be substituted and preferably are unsubstituted.

Compounds of Formula II in which the variables have the following meanings, which can be chosen independently of each other, are further preferred:

X, Y independently of each other in each case are O, N—R$^{11}$, wherein R$^{11}$ is a branched or unbranched C$_1$-C$_{16}$ alkyl radical;

R$^1$, R$^2$ independently of each other in each case are a methyl group, which can be substituted by one or more fluorine atoms;

R$^5$, R$^6$ independently of each other in each case are COOH, CH$_2$OH, CO—NH$_2$, CH$_2$—NH$_2$ or R$^5$ and R$^6$ together form a —C(=O)—O—C(=O)— or —(CH$_2$)$_n$— group, wherein n is 3 or 4 and one or more, preferably all H atoms can be replaced by F, particularly preferably R$^5$ and R$^6$ together form a —(CF$_2$)$_3$— group;

R$^a$, R$^b$, R$^c$, R$^d$ and R$^{a\prime}$, R$^{b\prime}$, R$^{c\prime}$, R$^{d\prime}$ independently of each other are H, halogen, a branched or unbranched C$_1$-C$_{16}$ alkyl radical, —O-alkyl, wherein alkyl stands for a branched or unbranched C$_1$-C$_{16}$ alkyl radical and wherein all alkyl radicals can be substituted by one or more fluorine atoms, wherein the radicals R$^a$, R$^b$, R$^c$, R$^d$ and/or the radicals R$^{a\prime}$, R$^{b\prime}$, R$^{c\prime}$, R$^{d\prime}$ can be linked to each other, forming one or more aromatic rings, which are preferably not substituted.

Compounds of Formula II are also called diarylethenes in the following.

Preferred compounds of Formulae I and II are:

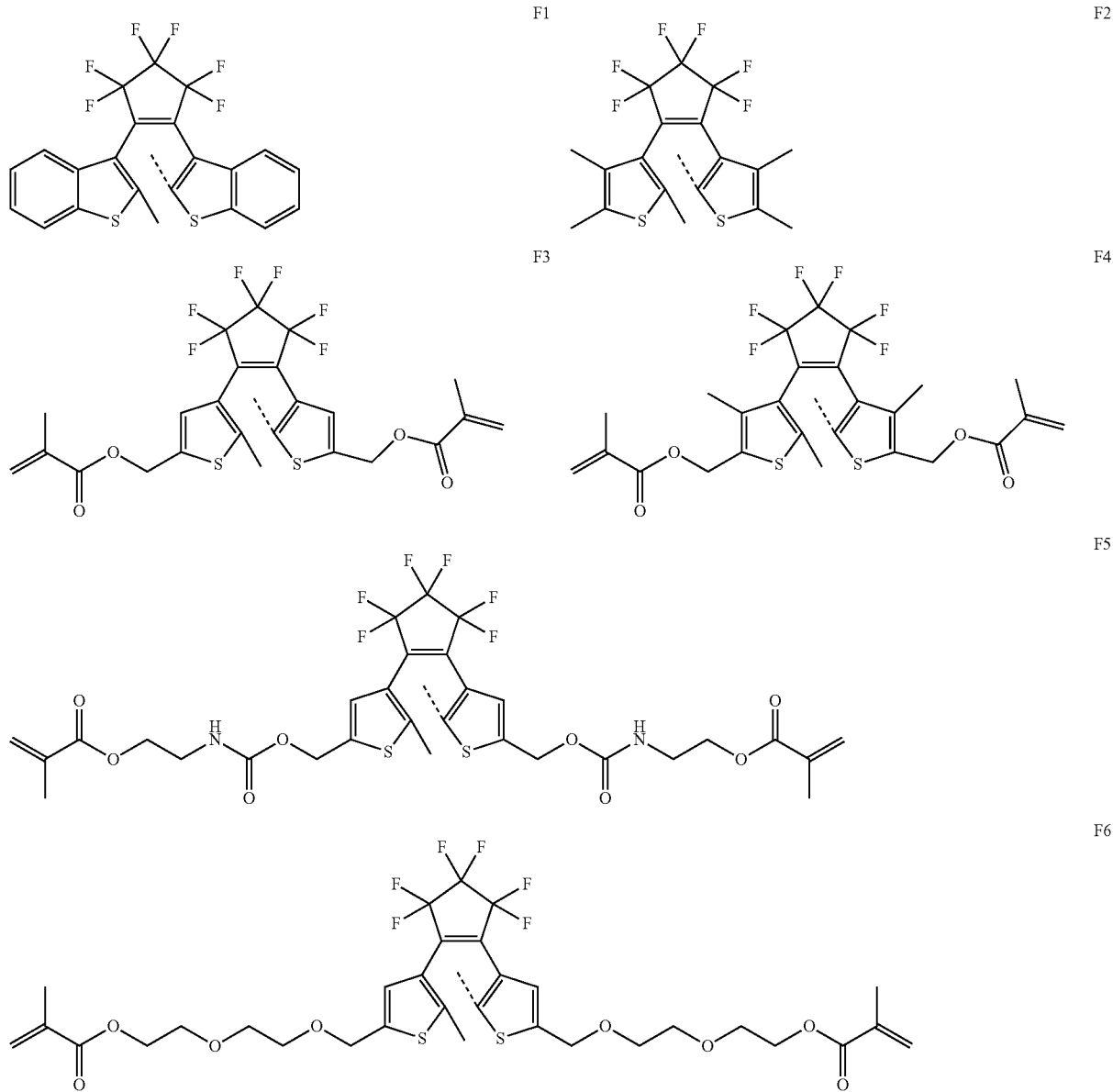

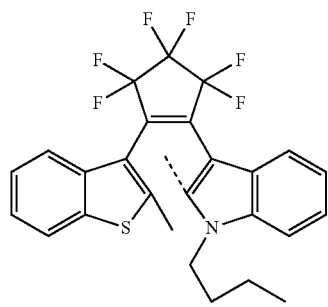

F7

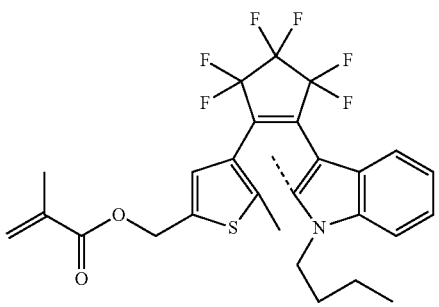

F8

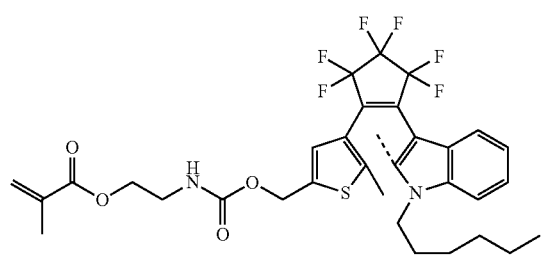

F9

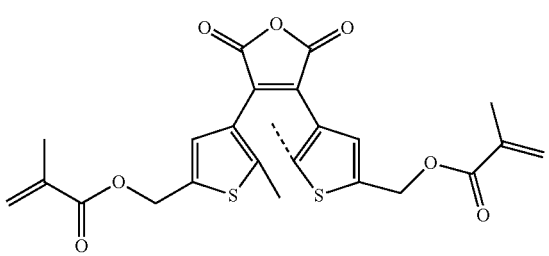

F10

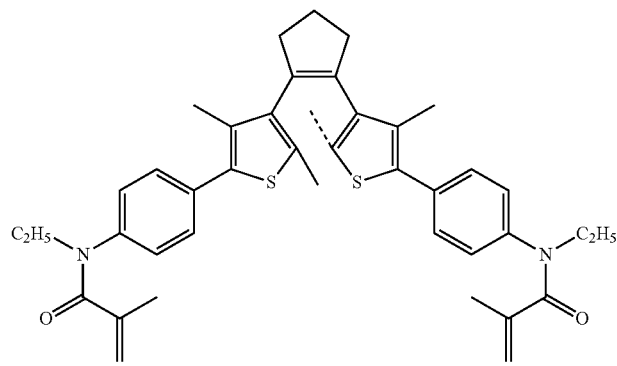

F11

In all cases, compounds of Formulae I and II which carry one or more radically polymerizable groups, in particular vinyl, (meth)acryl and/or (meth)acrylamide groups are particularly preferred. Such compounds are covalently incorporated into the organic polymer matrix during the radical hardening of the dental materials and then can no longer be washed out, with the result that the photochromic properties are also preserved over longer periods of time. Furthermore, the ability to migrate is substantially reduced in this way.

The compounds of Formulae I and II used according to the invention are characterized by a reversible light-induced colouring at different wavelengths, i.e. they can be coloured by brief irradiation with light of the wavelength $\lambda_1$ and decoloured again by irradiation with light of the wavelength $\lambda_2$, wherein the decolouration is preferably effected with longer-wave visible light. This procedure surprisingly proceeds highly efficiently, even when the compounds of Formula I or II are embedded in amorphous polymer networks, so-called polymer glasses, by copolymerization. According to the invention, compounds of Formulae I and II in which $\lambda_2 > \lambda_1 + 50$ nm are preferred. $\lambda_1$ preferably lies in the ultraviolet range and $\lambda_2$ in the visible spectral range. Here, $\lambda_1$ is to be chosen such that, during irradiation, the photoinitiator contained in the material and the compound I do not affect each other substantially in terms of functionality. The incorporation of I into the dental varnish does not result in a visible discolouration of the seal.

The compounds of Formulae I and II are P-type chromophores. Dental materials which contain a compound of Formulae I and II can be decoloured in a targeted manner by irradiation with light of the wavelength $\lambda 2$. This makes a high degree of flexibility in the processing of the materials possible, because the processing time can be chosen as desired, unlike with T-type chromophores.

The dental materials according to the invention based on photochromic additives of general formulae I and II can thus be coloured or made visible in a targeted manner by brief irradiation with light of the wavelength $\lambda_1$. The coloured dental materials can then be decoloured again by brief irradiation, in the range of seconds, with light of the wavelength $\lambda_2$. The reactions proceeding here are shown by way of example for Formula II:

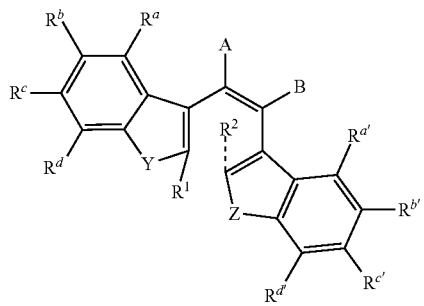
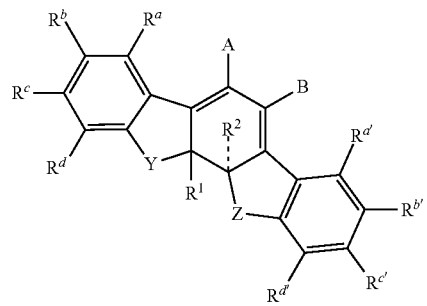

The uncoloured compounds are characterized by an open ring (left-hand formula), the coloured compounds by a closed ring (right-hand formula). The materials according to the invention are preferably sold in the uncoloured form, and the compounds of Formulae I and II are accordingly defined here using the formulae for the uncoloured compounds. However, it goes without saying that those materials which contain the corresponding coloured compounds are also a subject of the invention.

The colour effect which can be achieved depends mainly on the concentration of photochromic compound of Formula I or II, the degree of transformation, the rate of transformation and the extinction coefficient of the photochemically produced compound. Compounds which have a quantum yield of more than 10% are preferred. The extinction coefficient preferably lies above 10,000 $M^{-1}$ $cm^{-1}$.

According to the invention, those compounds of Formulae I and II are preferred which can be excited with a wavelength $\lambda_1$ smaller than 400 nm, in particular with UV light in the range of 320-395 nm, wherein those compounds which have no or only a slight intrinsic colour are particularly preferred. The compounds of Formulae F1-F11 meet these requirements.

Commercially available photochromic compounds with a diarylethene structure (according to Formulae I and II) are:

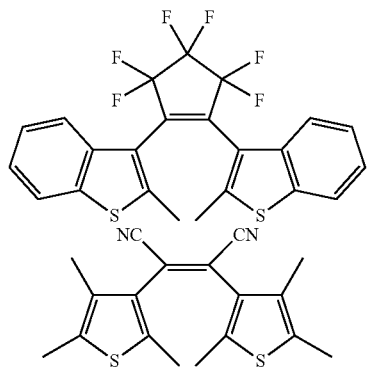

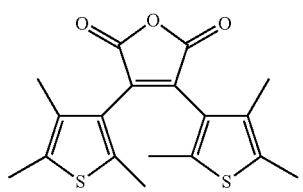

-continued

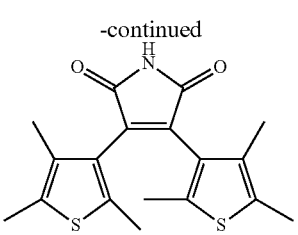

The dental materials according to the invention contain, in addition to the monomers of general formula I, preferably additionally further radically polymerizable monomers, in particular mono- and/or polyfunctional (meth)acrylic acid derivatives. Materials which contain at least one multifunctional (meth)acrylate or a mixture of mono- and multifunctional (meth)acrylates as radically polymerizable monomer are particularly preferred. By monofunctional (meth)acrylates is meant compounds with one, by polyfunctional (meth)acrylates is meant compounds with two or more, preferably 2 to 4, radically polymerizable groups. According to a quite particularly preferred embodiment, the compositions according to the invention contain at least one dimethacrylate or a mixture of mono- and dimethacrylates. Materials which contain mono- and multifunctional (meth)acrylates as radically polymerizable monomer are particularly suitable as dental materials. In all cases, methacrylates are preferred as comonomers. It was found that the monomers of Formula I and in particular the preferred compounds of Formula I with the comonomers named here have good compatibility and form homogeneous mixtures which, in the case of polymerization, produce materials with very good mechanical properties.

Preferred mono- or polyfunctional methacrylates are methyl, ethyl, hydroxyethyl, butyl, benzyl, tetrahydrofurfuryl or isobornyl(meth)acrylate, p-cumylphenoxyethylene glycol methacrylate (CMP-1E), bisphenol A di(meth)acrylate, bis-GMA (an addition product of methacrylic acid and bisphenol A diglycidylether), UDMA (an addition product of 2-hydroxyethyl methacrylate (HEMA) and 2,2,4-trimethylhexamethylene diisocyanate), TMX-UDMA (an addition product of a mixture of HEMA and hydroxypropyl methacrylate (HPMA) with α,α,α',α'-tetramethyl-m-xylylene diisocyanate (TMXDI)), bis(meth-acryloyloxymethyl)tricyclo[5.2.1.]decane (TCDMA), ethoxylated or propoxylated bisphenol A di(meth)acrylate, such as e.g. the bisphenol A dimethacrylate 2-[4-(3-methacryloyloxyethoxy-ethyl)phenyl]-2-[4-(3-methacryloyloxyethyl)phenyl]-propane) (SR-348c) with 3 ethoxy groups or 2,2-bis[4-(2-(meth)acryloxypropoxy)phenyl]propane, di-, tri- or tetraethylene glycol di(meth)acrylate, trimethylolpropane tri(meth)acrylate, pentaerythritol tetra(meth)acrylate, as well as glycerol di(meth)

acrylate, 1,4-butanediol di(meth)acrylate, 1,10-decanediol di(meth)acrylate or 1,12-dodecanediol di(meth)-acrylate or glycerol trimethacrylate (GTMA).

N-mono- or -disubstituted acrylamides, such as e.g. N-ethyl acrylamide, N,N-dimethyl acrylamide, N-(2-hydroxyethyl)acrylamide or N-methyl-N-(2-hydroxyethyl) acrylamide, or N-monosubstituted methacrylamides, such as e.g. N-ethylmethacrylamide or N-(2-hydroxyethyl)ethacrylamide as well as N-vinylpyrrolidone are further preferred. These monomers are characterized by a low viscosity and a high hydrolytic stability and are particularly suitable as diluting monomers.

Crosslinking pyrrolidones, such as e.g. 1,6-bis(3-vinyl-2-pyrrolidonyl)-hexane or commercially available bisacrylamides, such as methylene- or ethylenebisacrylamide, or bis(meth)acrylamides, such as e.g. N,N'-diethyl-1,3-bis(acrylamido)-propane, 1,3-bis(methacrylamido)-propane, 1,4-bis(acrylamido)-butane or 1,4-bis(acryloyl)piperazine, which can be synthesized by reaction from the corresponding diamines with (meth)acrylic acid chloride, are also preferred. These monomers are characterized by a high hydrolytic stability and are particularly suitable as crosslinking monomers.

Alternatively or in addition, the dental materials according to the invention can contain, in addition to the comonomers named above, one or more acid-group-containing radically polymerizable monomers (adhesive monomers) as additional monomers. These give the materials self-adhesive and/or self-etching properties.

The compounds of Formulae I and II are stable under acidic conditions and can be converted to the coloured ring-closed form with UV light. The reverse reaction with visible light likewise proceeds reversibly.

Preferred acid-group-containing monomers are polymerizable carboxylic acids, phosphonic acids, phosphoric acid esters and sulphonic acids.

Preferred carboxylic acids are maleic acid, acrylic acid, methacrylic acid, 2-(hydroxymethyl)acrylic acid, 4-(meth)-acryloyloxyethyltrimellitic acid, 10-methacryloyloxydecyl-malonic acid, N-(2-hydroxy-3-methacryloyloxypropyl)-N-phenyl-glycine and 4-vinylbenzoic acid.

Preferred phosphonic acid monomers are vinyl phosphonic acid, 4-vinylphenyl phosphonic acid, 4-vinylbenzyl phosphonic acid, 2-methacryloyloxyethyl phosphonic acid, 2-methacrylamidoethyl phosphonic acid, 4-methacrylamido-4-methylpentyl phosphonic acid, 2-[4-(dihydroxyphosphoryl)-2-oxa-butyl]-acrylic acid or 2-[4-(dihydroxyphosphoryl)-2-oxa-butyl]-acrylic acid ethyl and -2,4,6-trimethyl phenyl ester.

Preferred acidic polymerizable phosphoric acid esters are 2-methacryloyloxypropyl mono- or dihydrogen phosphate, 2-methacryloyloxyethyl mono- or dihydrogen phosphate, 2-methacryl-oyloxyethylphenyl hydrogen phosphate, dipentaerythritol penta-methacryloyloxy phosphate, 10-methacryloyloxydecyl dihydrogen phosphate, phosphoric acid mono-(1-acryloyl-piperidin-4-yl) ester, 6-(methacrylamido) hexyl dihydrogen phosphate and 1,3-bis-(N-acryloyl-N-propyl-amino)-propan-2-yl dihydrogen phosphate.

Preferred polymerizable sulphonic acids are vinyl sulphonic acid, 4-vinylphenyl sulphonic acid or 3-(methacrylamido)propylsulphonic acid.

Particularly preferred acid monomers are 4-(meth)acryloyloxyethyltrimellitic anhydride, 10-methacryloyloxydecylmalonic acid, 2-methacryloyloxyethyl phosphonic acid, 2-methacrylamidoethyl phosphonic acid, 2-[4-(dihydroxyphosphoryl)-2-oxa-butyl]acrylic acid, 2-[4-(dihydroxyphosphoryl)-2-oxa-butyl]-acrylic acid ethyl or -2,4,6-trimethyl phenyl ester, 2-methacryloyloxypropyl mono- or dihydrogen phosphate, 2-methacryloyloxyethyl mono- or dihydrogen phosphate, 2-meth-acryloyloxyethylphenyl hydrogen phosphate, 10-methacryloyloxydecyl dihydrogen phosphate, 6-(methacrylamido)hexyl dihydrogen phosphate and 1,3-bis-(N-acryloyl-N-propyl-amino)-propan-2-yl dihydrogen phosphate.

The dental materials according to the invention preferably also contain an initiator for the radical polymerization.

Benzophenone, benzoin and derivatives thereof or α-diketones or derivatives thereof, such as 9,10-phenanthrenequinone, 1-phenyl-propane-1,2-dione, diacetyl or 4,4'-dichlorobenzil are preferred for the initiation of the radical photopolymerization. Camphorquinone and 2,2-dimethoxy-2-phenyl-acetophenone are particularly preferably used and α-diketones in combination with amines as reducing agent, such as e.g. 4-(dimethylamino)benzoic acid ethyl ester, N,N-dimethylamino-ethyl methacrylate, N,N-dimethyl-sym.-xylidine or triethanol-amine are particularly preferably used. Norrish type I photoinitiators, above all acyl- or bisacylphosphine oxides, monoacyltrialkyl or diacyldialkyl germanium compounds, such as e.g. benzoyltrimethylgermanium, dibenzoyldiethylgermanium or bis(4-methoxybenzoyl)diethylgermanium are also particularly suitable. Advantageously, mixtures of the different photoinitiators can also be used, such as e.g. dibenzoyldiethylgermanium in combination with camphorquinone and 4-dimethyl-amino-benzoic acid ethyl ester.

Preferably, redox-initiator combinations, such as e.g. combinations of benzoyl peroxide with N,N-dimethyl-sym.-xylidine or N,N-dimethyl-p-toluidine, are used as initiators for a polymerization carried out at room temperature. In addition, redox systems consisting of peroxides or hydroperoxides and such reducing agents, as e.g. ascorbic acid, barbiturates, thioureas or sulphinic acids, are also particularly suitable.

Furthermore, the dental materials according to the invention preferably also contain at least one organic or particularly preferably inorganic particulate filler. Fillers based on oxides such as $SiO_2$, $ZrO_2$ and $TiO_2$ or mixed oxides of $SiO_2$, $ZrO_2$, ZnO and/or $TiO_2$, nanoparticulate or microfine fillers such as pyrogenic silicic acid or precipitated silicic acid (weight-average particle size of 10-1000 nm) as well as mini fillers such as quartz, glass ceramic or X-ray opaque glass powders of e.g. barium or strontium aluminium silicate glasses (weight-average particle size of 0.2-10 µm) are preferred. Further preferred fillers are X-ray opaque fillers, such as ytterbium trifluoride or nanoparticulate tantalum(V) oxide or barium sulphate or mixed oxides of $SiO_2$ with ytterbium(III) oxide or tantalum(V) oxide (weight-average particle size of 10-1000 nm).

To improve the bond between the filler particles and the crosslinked polymerization matrix, $SiO_2$-based fillers can be surface-modified with methacrylate-functionalized silanes, such as e.g. 3-methacryloyloxypropyltrimethoxysilane. For the surface-modification of non-silicate fillers, e.g. of $ZrO_2$ or $TiO_2$, functionalized acidic phosphates, such as e.g. 10-methacryloyloxy dihydrogen phosphate can also be used.

Depending on the desired intended use, the dental materials according to the invention can preferably also contain a solvent, in particular water, ethanol or a mixture thereof.

Optionally, the compositions used according to the invention can also contain further additives, above all stabilizers, such as e.g. polymerization stabilizers, flavourings, colourants, microbiocidal active ingredients, fluoride-ion-releasing additives, optical brighteners, fluorescent agents, plasticizers and/or UV absorbers.

According to the invention, those dental materials which contain the following components are preferred:
a) 0.0001 to 5.0 wt.-%, preferably 0.001 to 3.0 wt.-% and particularly preferably 0.01 to 1.0 wt.-% of at least one compound of general formula I,
b) 0.01 to 10 wt.-%, particularly preferably 0.1 to 3.0 wt.-% of at least one initiator, and optionally
c) 0 to 80 wt.-%, preferably 0 to 60 wt.-% and particularly preferably 5 to 50 wt.-% other monomer(s), and optionally
d) 0 to 80 wt.-% filler(s), and optionally
e) 0 to 70 wt.-% solvent.

Dental materials for use as cement or filling composite preferably have the following composition:
a) 0.0001 to 5.0 wt.-%, preferably 0.001 to 3.0 wt.-% and particularly preferably 0.01 to 1.0 wt.-% of at least one compound of general formula I,
b) 0.01 to 10 wt.-%, particularly preferably 0.1 to 3.0 wt.-% of at least one initiator,
c) 0 to 50 wt.-%, preferably 0 to 40 wt.-% and particularly preferably 5 to 40 wt.-% other monomer(s),
d) 10 to 80 wt.-%, preferably 20 to 80 wt.-%, particularly preferably 30 to 80 wt.-% filler(s).

Dental materials for use as adhesives or coating material preferably have the following composition:
a) 0.0001 to 5.0 wt.-%, preferably 0.001 to 3.0 wt.-% and particularly preferably 0.01 to 1.0 wt.-% of at least one compound of general formula I,
b) 0.01 to 10 wt.-%, particularly preferably 0.1 to 3.0 wt.-% of at least one initiator,
c) 0 to 80 wt.-%, preferably 5 to 60 wt.-% and particularly preferably 5 to 50 wt.-% other monomer(s),
d) 0 to 20 wt.-% filler(s),
e) 0 to 70 wt.-%, preferably 0 to 60 wt.-% and particularly preferably 0 to 50 wt.-% solvents, in particular water and/or ethanol.

Dental materials for the production of prostheses or artificial teeth preferably have the following composition:
a) 0.0001 to 5.0 wt.-%, preferably 0.001 to 3.0 wt.-% and particularly preferably 0.01 to 1.0 wt.-% of at least one compound of general formula I,
b) 0.01 to 10 wt.-%, particularly preferably 0.1 to 3.0 wt.-% of at least one initiator, and
c) 0 to 80 wt.-%, preferably 0 to 60 wt.-% and particularly preferably 5 to 50 wt.-% other monomer(s), and
d) 0 to 40 wt.-% filler(s).

Dental materials for the production of inlays, onlays, crowns or bridges preferably have the following composition:
a) 0.0001 to 5.0 wt.-%, preferably 0.001 to 3.0 wt.-% and particularly preferably 0.01 to 1.0 wt.-% of at least one compound of general formula I,
b) 0.01 to 10 wt.-%, particularly preferably 0.1 to 3.0 wt.-% of at least one initiator, and optionally
c) 0 to 60 wt.-%, preferably 0 to 50 wt.-% and particularly preferably 5 to 50 wt.-% other monomer(s), and optionally
d) 10 to 80 wt.-%, preferably 15 to 80 wt.-% and particularly preferably 20 to 80 wt.-% filler(s).

Unless otherwise stated, all quantities relate to the total mass of the materials. The individual quantity ranges can be chosen separately.

Those materials which consist of the named components are particularly preferred. Furthermore, those materials in which the individual components are in each case selected from the above-named preferred and particularly preferred substances are preferred.

The materials according to the invention are particularly suitable as dental materials, in particular as dental cements, filling composites and veneering materials and as materials for the production of prostheses, artificial teeth, inlays, onlays, crowns and bridges. They are characterized by reversible photochromic properties.

The dental materials are suitable primarily for intraoral application by the dentist to restore damaged teeth (clinical materials), i.e. for therapeutic use, e.g. as dental cements, filling composites and veneering materials. However, they can also be used extraorally, for example in the production or repair of dental restorations, such as prostheses, artificial teeth, inlays, onlays, crowns and bridges (technical materials).

The invention is explained in more detail below by means of embodiment examples.

EMBODIMENT EXAMPLES

Example 1

Methacrylate Resin and Fissure Sealant Based on a Photochromic Additive

The following compositions (proportions in wt.-%) were prepared in a mixing bowl (resin) or with a three roll mill (Table 1):

TABLE 1

Composition of the materials [wt. - %]

| Component | Resin | Fissure sealant |
|---|---|---|
| Bis-GMA | 19.90 | 11.98 |
| UDMA | 39.44 | 23.74 |
| TEGDMA[1] | 39.66 | 23.54 |
| CQ[2] | 0.10 | 0.06 |
| EDMAB[3] | 0.40 | 0.24 |
| B2287[4] | 0.50 | 0.50 |
| Aerosil Ox-50[5] | — | 15.64 |
| HDK 2000[6] | — | 4.00 |
| Glass filler[7] | — | 20.30 |

[1]Triethylene glycol dimethacrylate
[2]Camphorquinone
[3]p-Dimethylamino-benzoic acid ethyl ester
[4]Photochromic additive: 1,2-bis[2-methylbenzo-[b]thiophen-3-yl]-3,3,4,4,5,5-hexafluoro-1-cyclopentene (TCI Europe):

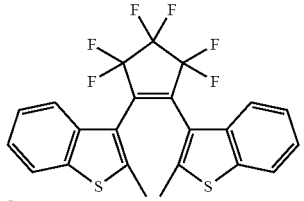 [SMILES: Cc1sc2ccccc2c1C1=C(c2c(C)sc3ccccc23)C(F)(F)C(F)(F)C1(F)F]

[5]Silanized pyrogenic silicic acid (Degussa) with a specific surface area (BET) of approx. 50 m$^2$/g
[6]Pyrogenic silicic acid (Wacker) with a specific surface area (BET) of approx. 200 m$^2$/g
[7]Silanized glass ionomer filler G018-090 (Schott) with a particle diameter d$_{50}$ of 3 μm Round test pieces (diameter 10 mm, height: 1 mm) were prepared from the compositions and hardened for 2×1 minute with a dental light source (Spectramat®, Ivoclar Vivadent AG). Colourless (resin) or white (fissure sealant) test pieces which discoloured to pink when irradiated (2 s) with an LED ($\lambda_1$=385 nm) resulted. It was possible to decolour the test pieces again rapidly by irradiation (2 s) with an LED ($\lambda_2$=470 nm). The alternate discolouration and decolouration were able to be repeated at least 20× without restrictions.

Example 2

Synthesis of the Polymerizable Photochromic Compound 3,3,4,4,5,5-hexafluoro-1,2-bis(5-methacryloyloxymethyl-2-methyl-3-thienyl)cyclopent-1-ene

1st Stage: 4-Bromo-5-methylthiophene-2-carboxaldehyde

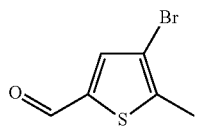

A solution of bromine (19.18 g; 0.12 mol) in acetic acid (50 ml) was added dropwise to a solution of 5-methyl-2-thiophenecarboxaldehyde (12.62 g; 97.9 mmol) in acetic acid (80 ml) under exclusion of light. The temperature was kept below 30° C. by cooling in a water bath. The reaction mixture was stirred for 72 h at RT and then carefully poured into saturated aqueous $Na_2CO_3$ solution (500 ml). After the gas evolution had abated, diethyl ether (400 ml) was added and the phases were separated. The aqueous phase was extracted with diethyl ether (2×100 ml). The combined organic phases were washed with saturated aqueous $NaHCO_3$ solution (150 ml), dried over $Na_2SO_4$, filtered and concentrated on a rotary evaporator. The crude product was purified by means of column chromatography ($SiO_2$, n-hexane/ethyl acetate 9:1; $R_f$=0.47). 14.67 g (71.5 mmol; 73%) of a yellowish solid was obtained.

$^1$H-NMR ($CDCl_3$, 400 MHz): δ=2.48 (s, 3H; $CH_3$), 7.59 (s, 1H, =CH), 9.77 (s, 1H, CHO).

$^{13}$C-NMR ($CDCl_3$, 100.6 MHz): δ=15.9 ($CH_3$), 111.2 (=C), 138.7 (=CH), 140.1 (=C), 145.8 (=C), 181.6 (C=O).

2nd Stage: 4-Bromo-2-hydroxymethyl-5-methylthiophene

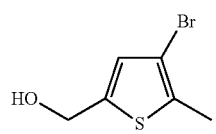

Sodium borohydride (5.36 g; 0.142 mol) was added to a solution of 4-bromo-5-methylthiophene-2-carboxaldehyde (24.20 g; 0.118 mol) in ethanol (250 ml) at 0° C. The reaction mixture was stirred for 1 h at 0° C. and for 2 h at ambient temperature. Then saturated aqueous $NH_4Cl$ solution (100 ml), water (200 ml) and ethyl acetate (300 ml) were added and the phases were separated. The aqueous phase was extracted with ethyl acetate (100 ml). The combined organic phases were washed with saturated aqueous $NaHCO_3$ solution (100 ml) and saturated aqueous NaCl solution (100 ml), dried over $Na_2SO_4$, filtered and concentrated on a rotary evaporator. The crude product was purified by means of column chromatography ($SiO_2$, n-hexane/ethyl acetate 4:1; $R_f$=0.35). 17.72 g (73%) of a yellowish liquid was obtained.

$^1$H-NMR ($CDCl_3$, 400 MHz): δ=2.35 (s, 3H; $CH_3$), 3.15 (t, 1H; J=4.4 Hz; OH), 4.60 (d, 2H; J=4.4 Hz; CH), 6.74 (s, 1H; =CH).

$^{13}$C-NMR ($CDCl_3$, 100.6 MHz): δ=14.7 ($CH_3$), 59.4 ($CH_2OH$), 108.2 (=C), 127.7 (=CH), 134.2 (=C), 140.8 (=C).

3rd Stage: (4-Bromo-5-methyl-thiophen-2-yl-methoxy)-tert.-butyldimethylsilane

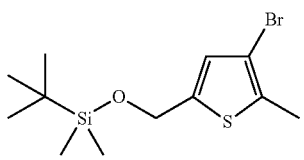 [SMILES: Cc1sc(CO[Si](C)(C)C(C)(C)C)cc1Br]

Imidazole (6.36 g; 93.5 mmol) was added to a solution of 4-bromo-2-hydroxymethyl-5-methylthiophene (17.60 g; 85.0 mmol) and tert.-butyldimethylchlorosilane (14.09 g; 93.5 mmol) in anhydrous dichloromethane (100 ml) and the suspension was stirred at RT. After 2 h, the reaction mixture was washed with diluted hydrochloric acid (1N; 100 ml), dried over $Na_2SO_4$, filtered and concentrated on a rotary evaporator. The crude product was dissolved in n-hexane (50 ml) and filtered over silica gel ($SiO_2$, n-hexane). The filtrate was concentrated on a rotary evaporator and the residue was dried under fine vacuum. 25.84 g (95%) of a colourless oil was obtained.

$^1$H-NMR ($CDCl_3$, 400 MHz): δ=0.11 (s, 6H; Si—$CH_3$), 0.93 (s, 9H; C—$CH_3$), 2.36 (s, 3H; $CH_3$), 4.75 (s, 2H; O—$CH_2$), 6.70 (s, 1H; =CH).

$^{13}$C-NMR ($CDCl_3$, 100.6 MHz): δ=−5.3 ($CH_3$), 14.7 ($CH_3$), 18.3 (C), 25.8 ($CH_3$), 60.5 ($CH_2$), 107.9 (=C), 126.0 (=CH), 133.1 (=C), 142.2 (=C).

$^{29}$Si-NMR ($CDCl_3$, 79.5 MHz): δ=21.6.

4th Stage: 3,3,4,4,5,5-Hexafluoro-1,2-bis((tert.-butyldimethvl-silyl)oxymethyl-2-methyl-3-thienyl)cyclopent-1-ene

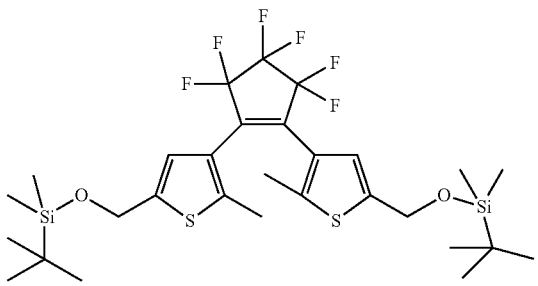 [SMILES: Cc1sc(CO[Si](C)(C)C(C)(C)C)cc1C1=C(c2cc(CO[Si](C)(C)C(C)(C)C)sc2C)C(F)(F)C(F)(F)C1(F)F]

A solution of (4-bromo-5-methyl-thiophen-2-ylmethoxy)-tert.-butyldimethylsilane (25.74 g; 80.0 mmol) in anhydrous tetrahydrofuran (100 ml) under argon was cooled to −75° C. n-Butyllithium (2.5M in n-hexane; 32.6 ml; 82.0 mmol) was added dropwise and the yellow solution was stirred for 2 h at −75° C. Octafluorocyclopentene (8.48 g; 40.0 mmol) was added and the reaction mixture was stirred overnight in a thawing cold bath. After 20 h, water (100 ml) and ethyl acetate (300 ml) were added to the reaction mixture and the phases were separated. The organic phase was washed with water (2×100 ml). The combined aqueous phases were re-extracted with ethyl acetate (100 ml). The combined organic phases were washed with saturated aqueous NaCl solution (100 ml), dried over $Na_2SO_4$, filtered and concentrated on a rotary evaporator. The crude product was purified by means of column chromatography ($SiO_2$, n-hexane/ethyl acetate 20:1; $R_f$=0.63). 19.46 g (74%) of a brownish liquid was obtained.

$^1$H-NMR ($CDCl_3$, 400 MHz): δ=0.11 (s, 12H; Si—$CH_3$), 0.94 (s, 18H; C—$CH_3$), 1.88 (s, 6H; $CH_3$), 4.80 (s, 4H; O—$CH_2$), 6.87 (s, 2H; =CH).

$^{13}$C-NMR ($CDCl_3$, 100.6 MHz): δ=−5.3 ($CH_3$), 14.4 ($CH_3$), 18.3 (C), 25.8 ($CH_3$), 60.6 ($CH_2$), 111.1 (m; $CF_2$), 113.7 (m; $CF_2$), 116.2 (m; $CF_2$), 118.8 (m; $CF_2$), 123.1 (=CH), 124.3 (=C), 135.8 (m, =C—CF), 141.1 (=C), 143.5 (=C).

$^{19}$F-NMR ($CDCl_3$, 376.5 MHz): δ=−131.9 (2F), −110.0 (4F).

$^{29}$Si-NMR ($CDCl_3$, 79.5 MHz): δ=21.7.

5$^{th}$ Stage: 3,3,4,4,5,5-hexafluoro-1,2-bis(5-hydroxymethyl-2-methyl-3-thienyl)cyclopent-1-ene

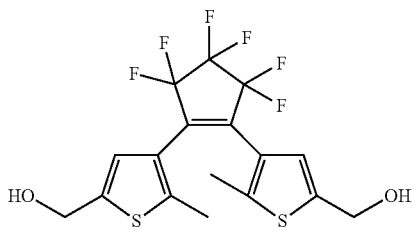 [SMILES: Cc1sc(CO)cc1C1=C(c2cc(CO)sc2C)C(F)(F)C(F)(F)C1(F)F]

Tetrabutyl ammonium fluoride (75% in water; 25.00 g; 66.9 mmol) was added dropwise to a solution of 3,3,4,4,5,5-hexafluoro-1,2-bis[(tert.-butyldimethylsilyl)oxymethyl-2-methyl-3-thienyl)cyclopent-1-ene (19.20 g; 29.2 mmol) in tetrahydrofuran (100 ml). The reaction solution was stirred for 4 h at RT, then saturated aqueous $NH_4Cl$ solution (100 ml) and ethyl acetate (100 ml) were added and the phases were separated. The organic phase was washed with water (2×100 ml) and saturated aqueous NaCl solution (100 ml), dried over $Na_2SO_4$, filtered and concentrated on a rotary evaporator. The crude product was purified by means of column chromatography ($SiO_2$, n-hexane/ethyl acetate 1:1; $R_f$=0.38). 4.35 g (10.2 mmol; 35%) of a colourless solid was obtained.

1H-NMR ($CDCl_3$, 400 MHz): δ=1.87 (s, 6H; $CH_3$), 4.26 (s, 2H; OH), 4.68 (s, 4H; O—$CH_2$), 6.91 (s, 2H; =CH).

$^{13}$C-NMR ($CDCl_3$, 100.6 MHz): δ=14.3 ($CH_3$), 59.1 ($CH_2$), 110.8 (m; $CF_2$), 113.4 (m; $CF_2$), 116.0 (m; $CF_2$), 118.5 (m; $CF_2$), 124.0 (=CH), 135.7 (m, =C—$CF_2$), 141.4 (=C), 143.1 (=C).

$^{19}$F-NMR ($CDCl_3$, 376.5 MHz): δ=−131.9 (2F), −110.0 (4F).

6$^h$ Stage: 3,3,4,4,5,5-Hexafluoro-1,2-bis(5-methacryloyloxymethyl-2-methyl-3-thienyl)cyclopent-1-ene

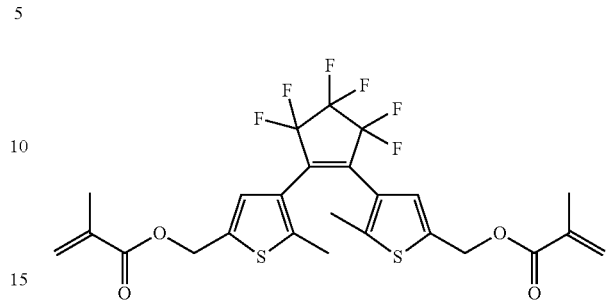

A solution of methacrylic anhydride (3.21 g; 20.8 mmol) in dichloromethane (20 ml) was added dropwise to a solution of 3,3,4,4,5,5-hexafluoro-1,2-bis(5-hydroxymethyl-2-methyl-3-thienyl)cyclopent-1-ene (4.25 g; 9.9 mmol), triethylamine (2.21 g; 21.8 mmol) and N,N-dimethylaminopyridine (0.24 g; 2.0 mmol) in anhydrous dichloromethane (80 ml) at −5° C. The reaction mixture was stirred for 3 h at −5° C. and then at ambient temperature. After 20 h, the solution was washed with water (3×100 ml) and saturated aqueous NaCl solution (100 ml), dried over $Na_2SO_4$, filtered and concentrated on a rotary evaporator. The crude product was purified by means of column chromatography ($SiO_2$, n-hexane/ethyl acetate 9:1; $R_f$=0.40). 4.68 g (8.3 mmol; 84%) of a colourless solid was obtained (m.p.: 58° C.).

$^1$H-NMR ($CDCl_3$, 400 MHz): δ=1.86 (s, 6H; $CH_3$), 1.95 (m, 6H; $CH_3$), 5.24 (s, 4H; O—$CH_2$), 5.61 (m, 2H; =CH), 6.14 (m, 2H; =CH); 7.05 (s, 2H; =CH).

$^{13}$C-NMR ($CDCl_3$, 100.6 MHz): δ=14.2 ($CH_3$), 18.2 ($CH_3$), 60.5 ($CH_2$), 110.9 (m; $CF_2$), 113.4 (m; $CF_2$), 116.0 (m; $CF_2$), 118.5 (m; $CF_2$), 124.3 (=C), 126.3 (=$CH_2$), 127.5 (=CH), 135.8 (=C), 136.1 (m, =C—$CF_2$), 136.4 (=C), 143.2 (=C), 166.9 (C=O).

$^{19}$F-NMR ($CDCl_3$, 376.5 MHz): δ=−131.9 (2F), −110.2 (4F). IR (neat): 2958 (w), 1716 (s), 1637 (m), 1561 (w), 1441 (m), 1404 (w), 1380 (w), 1337 (m), 1316 (m), 1273 (s), 1191 (m), 1136 (vs), 1109 (vs), 1046 (s), 1011 (m), 984 (vs), 942 (s), 898 (m), 856 (m), 813 (s), 740 (m), 709 (w), 656 (m), 635 (w) cm$^{-1}$.

Analysis calculated for $C_{25}H_{22}F_6O_4S_2$: C, 53.19; H, 3.93; S, 11.36.

Found: C, 53.20; H, 3.76; S, 11.10.

The invention claimed is:
1. A radically polymerizable dental material comprising at least one compound of Formula (I),

Formula I

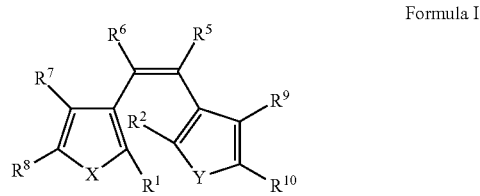

in which the variables have the following meanings:
X, Y in each case are S;
$R^1$, $R^2$ in each case are methyl;

$R^5;R^6$ together form a —$(CH_2)_n$— group, wherein n is 3 and wherein in the —$(CH_2)$— group one or more H atoms can be replaced by F;

$R^7,R^9$ independently of each other in each case are H or a $C_1$-$C_3$ alkyl radical;

$R^8, R^{10}$ independently of each other in each case are a $C_1$-$C_6$ alkyl radical, which can be interrupted by O or —O—C(=O)—NH— and which carries a terminal radically polymerizable group, wherein the polymerizable group is selected from vinyl, styryl, acrylate, methacrylate, acrylamide, N-alkylacrylamide, and methacrylamide, and at least one radically polymerizable monomer and at least one initiator for radical polymerization.

2. The dental material according to claim 1, in which the variables of Formula I have the following meanings:

X, Y in each case are S;

$R^1,R^2$ in each case are methyl;

$R^5;R^6$ together form a —$(CH_2)_n$— group, wherein n is 3 and wherein all H atoms are replaced by F;

$R^7,R^9$ independently of each other in each case are H or a $C_1$-$C_3$ alkyl radical;

$R^8,R^{10}$ independently of each other in each case are a $C_1$-$C_6$ alkyl radical, which can be interrupted by O or —O—C(=O)—NH— and which carries a terminal methacrylate group.

3. The dental material according to claim 1, wherein the at least one radically polymerizable monomer is a mono- or polyfunctional (meth)acrylic acid derivative, and wherein the at least one initiator for the radical polymerization is a photoinitiator.

4. The dental material according to claim 1, which additionally comprises at least one particulate filler.

5. The dental material according to claim 1 for intraoral use to restore damaged teeth.

6. The dental material according to claim 5 for therapeutic use as dental cement, dental filling composite, dental adhesive or veneering material.

7. A photochromic dental material comprising a compound of Formula I, as defined in claim 1.

8. The dental material according to claim 1, which comprises
a) 0.01 to 1.0 wt.-% of the at least one compound of general formula I,
b) 0.1 to 3.0 wt.-% of the at least one initiator,
c) 5 to 50 wt.-% of the at least one radically polymerizable monomer, and optionally
d) 0 to 80 wt.-% filler(s), and optionally
e) 0 to 70 wt.-% solvent,
in each case relative to the total mass of the dental material.

9. The dental material according to claim 1 for use as dental cement or dental filling composite, which comprises
a) 0.01 to 1.0 wt.-% of the at least one compound of general formula I,
b) 0.1 to 3.0 wt.-% of the at least one initiator,
c) 5 to 40 wt.-% of the at least one radically polymerizable monomer,
d) 30 to 80 wt.-% filler(s),
in each case relative to the total mass of the dental material.

10. The dental material according to claim 1 for use as dental adhesive or coating material, which comprises
a) 0.001 to 3.0 wt.-% of the at least one compound of general formula I,
b) 0.1 to 3.0 wt.-% of the at least one initiator,
c) 5 to 60 wt.-% of the at least one radically polymerizable monomer,
d) 0 to 20 wt.-% filler(s),
e) 0 to 60 wt.-% solvents, wherein the solvents comprise water and/or ethanol,
in each case relative to the total mass of the dental material.

11. The dental material according to claim 1 for use as dental adhesive or coating material, which comprises
a) 0.01 to 1.0 wt.-% of the at least one compound of general formula I,
b) 0.1 to 3.0 wt.-% of the at least one initiator,
c) 5 to 50 wt.-% of the at least one radically polymerizable monomer,
d) 0 to 20 wt.-% filler(s),
e) 0 to 50 wt.-% solvents, wherein the solvents comprise water and/or ethanol,
in each case relative to the total mass of the dental material.

* * * * *